(12) United States Patent
Furuya et al.

(10) Patent No.: US 7,419,480 B2
(45) Date of Patent: Sep. 2, 2008

(54) DISPOSABLE DIAPER

(75) Inventors: Kaori Furuya, Kagawa-ken (JP); Hironao Minato, Kagawa-ken (JP)

(73) Assignee: Uni-Charm Corporation (JP)

( * ) Notice: Subject to any disclaimer, the term of this patent is extended or adjusted under 35 U.S.C. 154(b) by 0 days.

(21) Appl. No.: 11/548,840

(22) Filed: Oct. 12, 2006

(65) Prior Publication Data

US 2007/0106241 A1    May 10, 2007

(30) Foreign Application Priority Data

Nov. 7, 2005    (JP) .............................. 2005-322567

(51) Int. Cl.
*A61F 13/15* (2006.01)

(52) U.S. Cl. .......................... 604/385.28; 604/385.227; 604/385.24; 604/385.26

(58) Field of Classification Search ............ 604/385.28, 604/385.27, 385.24, 385.26
See application file for complete search history.

(56) References Cited

U.S. PATENT DOCUMENTS

| | | |
|---|---|---|
| 3,929,135 A | 12/1975 | Thompson |
| 3,967,623 A | 7/1976 | Butterworth et al. |
| 4,029,101 A | 6/1977 | Chesky et al. |
| 4,341,217 A | 7/1982 | Ferguson et al. |
| 4,342,314 A | 8/1982 | Radel et al. |
| 4,636,207 A | 1/1987 | Buell |
| 4,695,278 A | 9/1987 | Lawson |
| 4,704,116 A | 11/1987 | Enloe |
| 4,738,677 A | 4/1988 | Foreman |
| 4,808,177 A * | 2/1989 | DesMarais et al. ..... 604/385.27 |
| 4,904,251 A | 2/1990 | Igaue et al. |
| 6,186,996 B1 | 2/2001 | Martin |

FOREIGN PATENT DOCUMENTS

| | | |
|---|---|---|
| EP | 0109126 A1 | 5/1984 |
| JP | 1-162807 | 6/1989 |
| JP | 1-213402 | 8/1989 |
| JP | 04-082977 A | 3/1992 |
| JP | 05003891 | 1/1993 |
| JP | 05-049659 A | 3/1993 |
| JP | 2003079659 | 3/2003 |
| WO | 93/02647 A1 | 2/1993 |
| WO | 95/15140 A1 | 6/1995 |

* cited by examiner

*Primary Examiner*—Jacqueline Stephens
(74) *Attorney, Agent, or Firm*—Lowe Hauptman Ham & Berner, LLP

(57) ABSTRACT

A disposable diaper has a pair of barrier cuffs. Each of the barrier cuffs includes inner and outer sheet strips provided separately of each other. The first and second sheet strips include bottom side edges fixed to the inner surface of the diaper and top side edges left free from the inner surface. The bottom side edge of the first sheet strip is inwardly spaced from the bottom side edge of the second sheet strip. The first and second sheet strips are locally bonded to each other in a part of the overlapping area of these sheet strips. One of the first and second sheet strips has its top side edge spaced from the top side edge of the other sheet strip and is provided with an elastic member.

5 Claims, 5 Drawing Sheets

DISPOSABLE DIAPER

BACKGROUND OF THE INVENTION

The present invention relates to a disposable diaper including a pair of elasticized barrier cuffs.

Disposable diapers including a pair of barrier cuffs elastically biased to be raised from the inner surface of the diaper have conventionally been well known. Specifically, such cuffs are raised from the inner surface of the diaper as elastic members attached in a stretched state to the diaper contract. Rising up in this manner, the cuffs function to prevent body fluid discharged on the inner surface of the diaper from leaking sideways.

For example, a disposable diaper disclosed in Japanese Unexamined Patent Application Publication No. 1989-162807 (REFERENCE 1) is provided in a crotch region with a pair of floating inner cuffs extending in a longitudinal direction. Each of these floating inner cuffs comprises a cuff layer defined by a part of topsheet, a base layer underlying the cuff layer and an elastic member sandwiched between the cuff layer and the base layer so as to extend in the longitudinal direction in a contractible manner. The elastic member is partially bonded to the base layer and the segment of the elastic member left free from the base layer functions to lift the cuff layer off from the base layer as this segment contracts. The cuff layer is bonded in its region a predetermined dimension spaced from the elastic member in a transverse direction of the diaper to the base layer. When lifted in this manner, the cuff layer describes an inverted V-shaped cross-section and thereby forms a double wall barrier cuff comprising walls lying inwardly and outwardly as viewed in a transverse direction of the diaper.

A disposable diaper disclosed in Japanese Unexamined Patent Application Publication No. 1989-213402 (REFERENCE 2) comprises a first sheet including side flaps put in close contact with the wearer's skin and a second sheet underlying the first sheet wherein each of the side flaps is provided in the vicinity of its outer side edge with a first elastic member and between the first elastic member and a liquid-absorbent core with a second elastic member. The first sheet is bonded in its two regions spaced from the second elastic member in opposite directions to the second sheet so that the first sheet may protuberate between these two regions as the second elastic member contracts. Consequentially, the first sheet forms a double wall barrier cuff comprising walls lying inwardly and outwardly as viewed in the transverse direction of the diaper.

The elasticized double wall barrier cuffs disclosed in REFERENCES 1 and 2 are respectively constructed in the manner that the elastic members are sandwiched between two sheets defining the inner walls and the outer walls as viewed in the transverse direction of the diaper, respectively, on transversely opposite lateral zones of the diaper so that these elastic members may lift the inner walls from below. According to such construction, a height of these barrier cuffs depends on the transversely opposite lateral zones of the diaper. It is desired to increase a height of the barrier cuffs, the transversely opposite lateral zones, particularly in the crotch region must be widened. However, any intention to widen a dimension of the crotch region is constrained by the essential condition for design. In order to increase a height of the barrier cuffs with the knowledge of such constraint, a width dimension of the body fluid absorbent core laid in the crotch region should be inevitably reduced. With the diaper having such narrow core, a capacity of the body fluid absorption in the crotch region is generally deteriorated. Therefore, it is an object of the present invention to solve the problem left behind unsolved by the prior art concerning the double wall barrier cuffs.

SUMMARY OF THE INVENTION

According to the present invention, there is a disposable diaper having a front waist region, a rear waist region and a crotch region. The disposable diaper comprises an inner surface put in contact with the wearer's skin and an outer surface put in contact with an undergarment and a body fluid absorbent core interposed between the inner and outer surfaces. The disposable diaper is formed on its inner surface with a pair of elastic barrier cuffs opposed to each other about a center line bisecting a width dimension of the crotch region so as to extend into the front and rear waist regions and adapted to be raised from the inner surface.

The present invention further comprises each of the barrier cuffs comprising inner and outer sheet strips in a form of sheet strips provided separately of each other, these first and second sheet strips respectively comprise bottom side edges fixed to the inner surface in the front and rear waist regions as well as in the crotch region and top side edges left free from the inner surface at least in the crotch region of the front waist region, the rear waist region and the crotch region. The bottom side edge of the first sheet strip is spaced aside from the bottom side edge of the second sheet strip toward the center line, the first and second sheet strips are collapsed onto the inner surface and overlap to each other in such collapsed state, and the first and second sheet strips are locally bonded in sections thereof extending in parallel to the center line to each other and one of these first and second sheet strips has its top side edge placed aside from the top side edge of the other sheet strip toward the center line while the top side edge of the other sheet strip is provided with an elastic member extending in parallel to the center line and bonded in a stretched state thereto.

According to other embodiment of the present invention, the top side edge of the one of said first and second sheet strips is also provided with an elastic member extending in parallel to the center line and bonded in a stretched state thereto.

According to another embodiment of the present invention, an intermediate section of the first sheet strip defined between a section over which the first sheet strip and the second sheet strip are bonded to each other and the bottom side edge of the first sheet strip is provided with an elastic member extending in parallel to the center line and bonded in stretched state thereto.

In the disposable diaper according to the present invention, each of the barrier cuffs comprises the first sheet strip and second sheet strip provided separately of the first sheet strip wherein the bottom side edge of the first sheet strip is spaced aside from the bottom side edge of the second sheet strip toward the center line. Such unique arrangement allows a height dimension of the barrier cuff to be increased by increasing a width dimension of at least one of the first and second sheet strips. The first and second sheet strips cooperate with the inner surface of the diaper to define a space and thereby to provide the double wall barrier cuff of which the second sheet strip functions as means to conceal contamination of the first sheet strip with body fluid.

According to the embodiment of the present invention wherein the first and second sheet strips are respectively provided along the top side edges thereof with the elastic members bonded in a stretched state thereto, the barrier cuff is more effectively raised up from the inner surface of the diaper than when only one of the first and second sheet strips is provided along its top side edge with the elastic member bonded in stretched state thereto. Consequentially, the respective top side edges can be elastically put in close contact with the wearer's skin.

According to the embodiment of the present invention wherein an intermediate section of the first sheet strip defined between a line along which the first sheet strip and the second sheet strip are bonded to each other and the bottom side edge of the first sheet strip is provided with the elastic member extending in parallel to the center line and bonded in stretched state thereto, the first sheet strip is formed with gathers in the vicinity of its intermediate section including this elastic member. These gathers function to prevent the first and second sheet strips from coming unacceptably close to each other and thereby to maintain the sufficiently large space between the first and second sheet strips.

DETAILED DESCRIPTION OF THE PREFERRED EMBODIMENTS

Details of a disposable diaper according to the present invention will be more fully understood from the description given hereunder with reference to the accompanying drawings.

Figure 1:
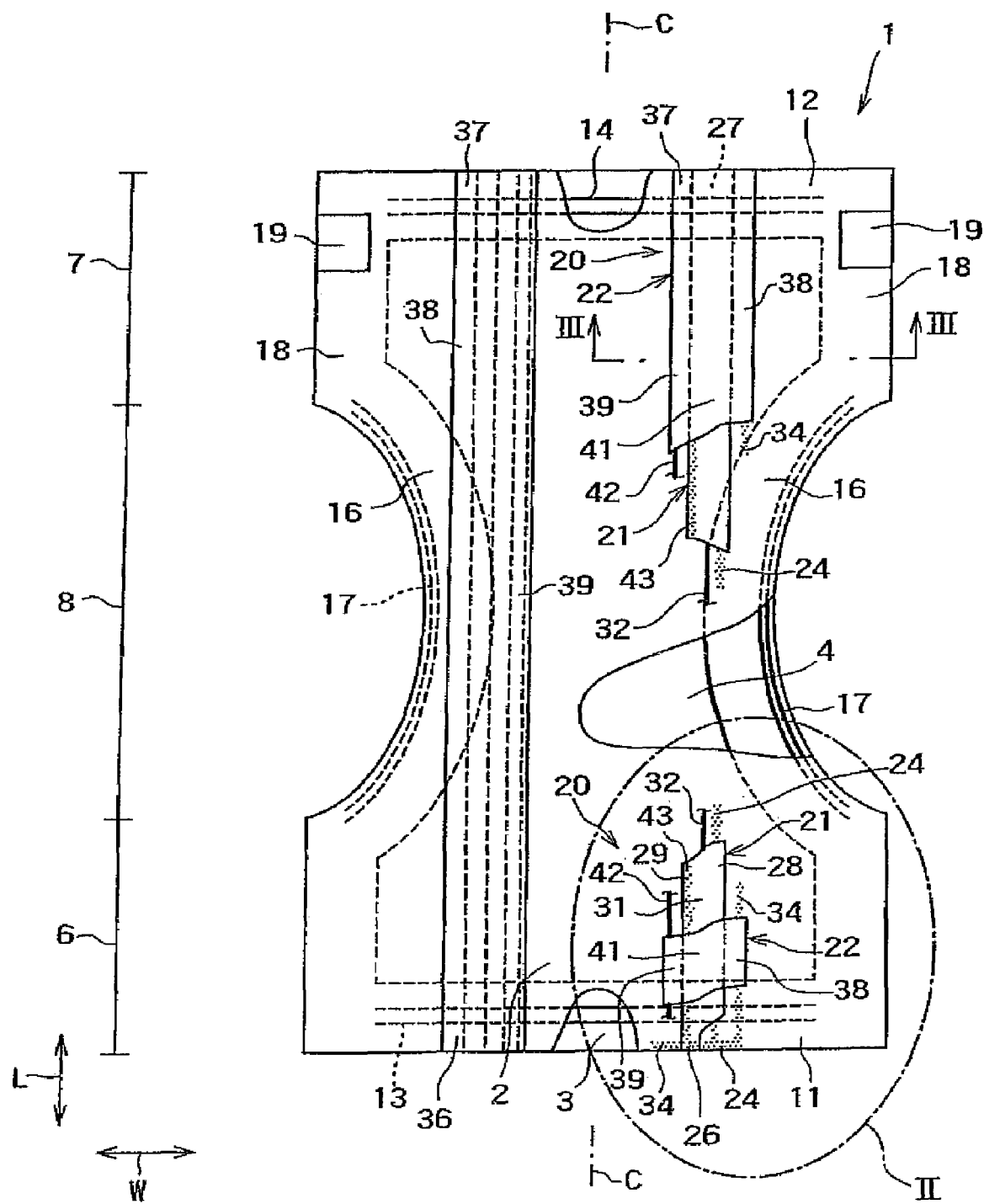
FIG. 1 is a partially cutaway plan view showing a disposable diaper according to the present invention.
Figure 2:
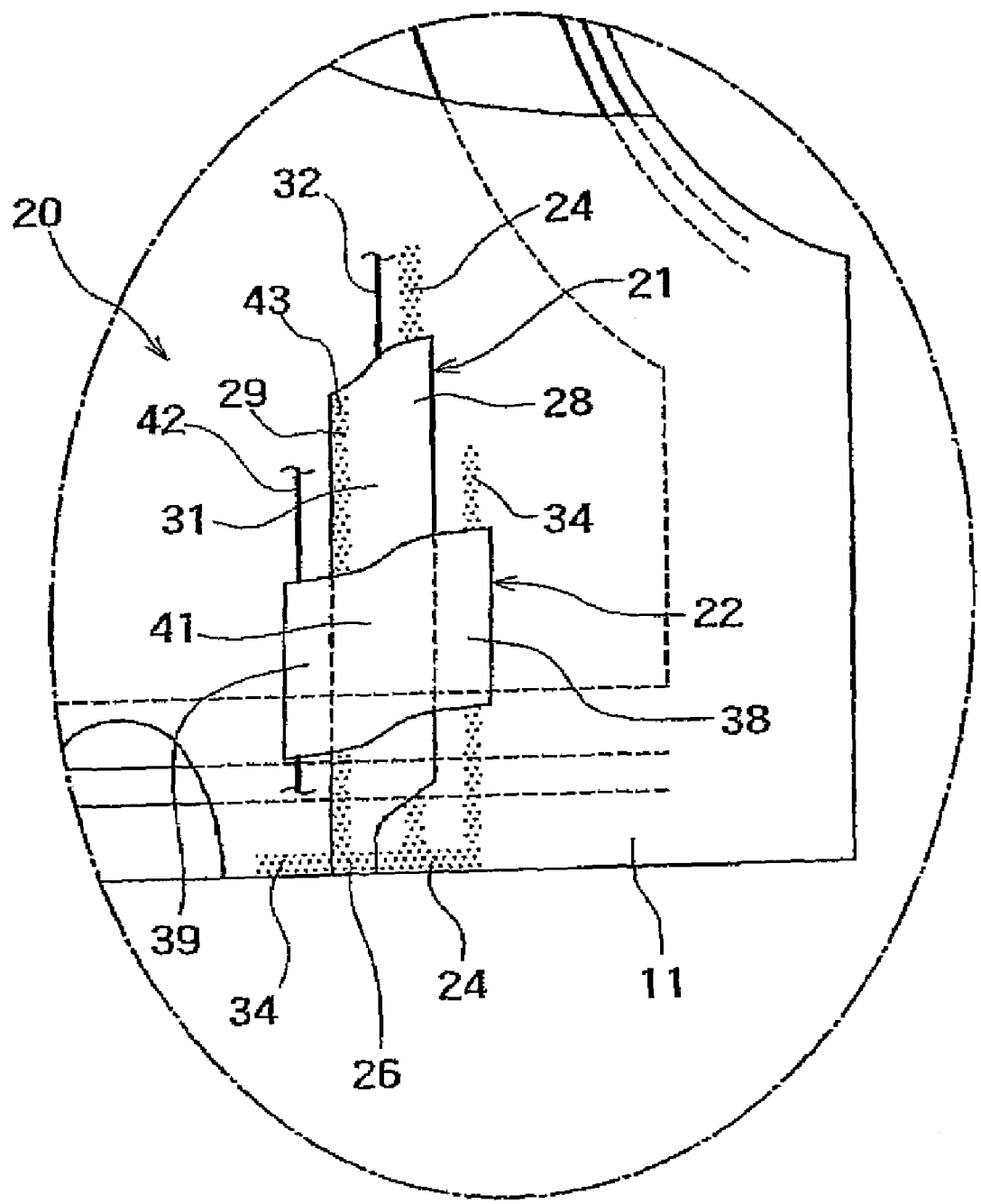
FIG. 2 is a plan view showing a part of FIG. 1 in an enlarged scale.

FIG. 1 is a partially cutaway plan view showing a disposable diaper 1 and FIG. 2 is a plan view showing a circled part II of FIG. 1 in an enlarged scale. The diaper 1 comprises a liquid-pervious topsheet 2 defining an inner surface put in contact with the wearer's skin, a liquid-impervious backsheet 3 defining an outer surface put in contact with clothes and a body fluid absorbent core 4 sandwiched between these two sheets 2, 3. The diaper 1 has a longitudinal direction L and a transverse direction W, defining a front waist region 6, a rear waist region 7 and a crotch region 8 extending between these two waist regions 6, 7 in the back-and-front direction L. The front and rear waist regions 6, 7 are respectively provided along respective ends 11, 12 thereof with waist elastic members 13, 14 sandwiched between the top- and backsheets 2, 3 and bonded in a stretched state to at least one of these sheets 2, 3. The crotch region 8 is provided along its transversely opposite side edges 16 with leg elastic members 17 sandwiched between the topsheet 2 and the backsheet 3 and bonded in a stretched state to at least one of these sheets 2, 3. The rear waist region 7 is provided on its transversely opposite side edges 18 with tape fasteners 19 used to connect the front and rear waist regions 6, 7 with each other. Paired barrier cuff 20 is laid on the inner surface of the diaper 1 on both sides of a center line C-C bisecting a width of the diaper 1, respectively.

Each of the barrier cuffs 20 comprises inner and outer sheets 21, 22 provided separately of each other placed upon each other and extending in the longitudinal direction L as seen in FIG. 1. The inner sheet 21 is of preferably liquid-impervious nature and bonded along front and rear ends 26, 27 and an outer side edge 28 thereof to the topsheet 2 by means of hot melt adhesive 24. An inner side edge 29 as well as an intermediate section 31 extending between the inner side edge 29 and the outer side edge 28 is not bonded to the topsheet 2 and an elastic member 32 exclusively for the intermediate section 31 extending in the longitudinal direction L is attached in a stretched state to the intermediate section 31 by means of hot melt adhesive (not shown). The outer sheet 22 also is preferably of liquid-impervious nature and bonded along front and rear ends 36, 37 and an outer side edge 38 thereof to the topsheet 2 and/or the inner sheet 21 overlapping the outer sheet 22 by means of hot melt adhesive 34. While the inner side edge 39 of the outer sheet 22 is bonded neither to the topsheet 2 nor to the inner sheet 21, an intermediate section 41 extending between the inner side edge 39 and the outer side edge 38 is bonded to the inner side edge 29 of the inner sheet 21 by means of hot melt adhesive 43. An elastic member 42 exclusively for the inner side edge 39 is attached in a stretched state to the inner side edge 39 by means of hot melt adhesive (not shown).

Figure 3:
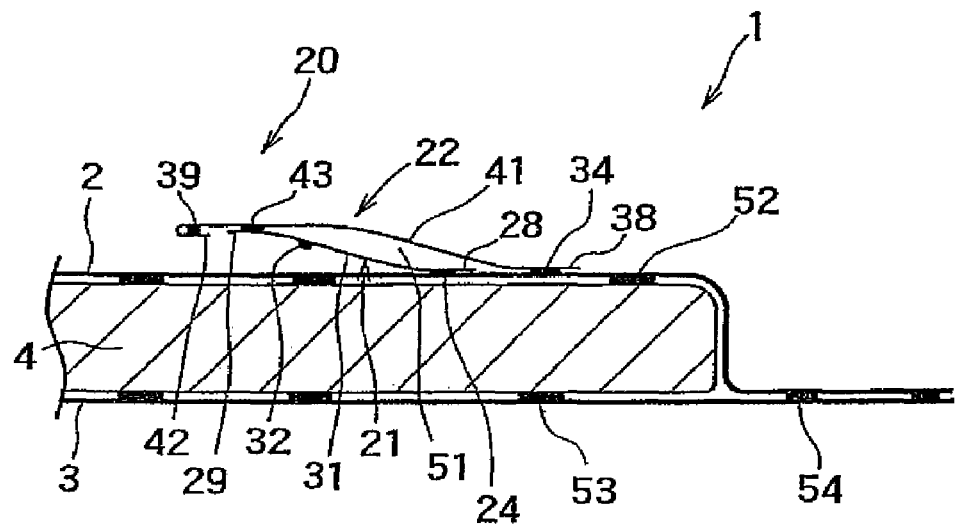
FIG. 3 is a sectional view taken along the line III-III in FIG. 1.

FIG. 3 is a sectional view taken along the line III-III in FIG. 1. For better understanding of the cross-sectional shape in question, the barrier cuff 20 is shown to be slightly raised from the topsheet 2 with the outer sheet 22 being slightly spaced from the inner sheet 21. The outer side edge 28 of the inner sheet 21 fixed to the topsheet 2 by means of adhesive 24 is placed aside toward the center line C (See FIG. 1) with respect to the outer side edge 38 of the outer sheet 22 fixed to the topsheet 2 by means of adhesive 34. The inner side edge 29 of the inner sheet 21 is bonded to the intermediate section 41 of the outer sheet 22 and the inner side edge 39 of the outer sheet 22 extends inward beyond the inner side edge 29 of the inner sheet 21 toward the center line C. Such barrier cuff 20 forms a space 51 surrounded by the inner sheet 21, the outer sheet 22 and the topsheet 2. As shown, the topsheet 2 and the backsheet 3 are bonded to the core 4 by means of hot melt adhesive 52, 53, respectively, and portions of these sheets 2, 3 extending outward beyond peripheral edge of the core 4 are bonded to each other by means of hot melt adhesive 54.

Figure 4:
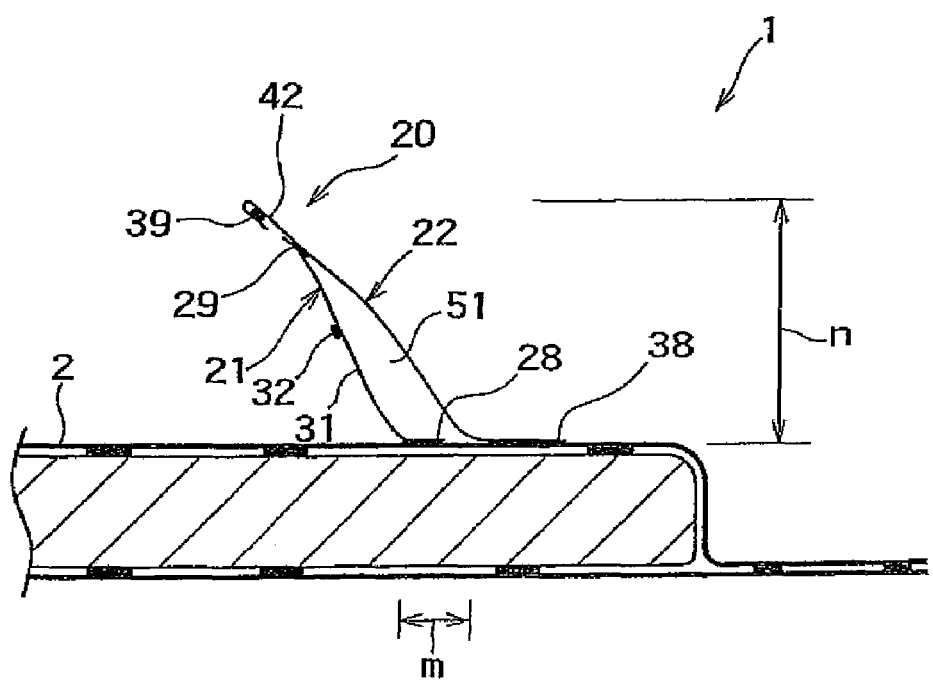
FIG. 4 is a view similar to FIG. 3, showing a posture taken by one of barrier cuffs when the disposable diaper bows.

FIG. 4 is a view similar to FIG. 3, showing a posture taken by one of the barrier cuffs 20 when the disposable diaper 1 of FIG. 1 bows in the longitudinal direction with the topsheet 2 inside. The barrier cuff 20 comes into the state substantially as shown when the diaper 1 is put on the wearer's body. Both the elastic member 42 exclusively for the inner side edge and the elastic member 32 exclusively for the intermediate section contract as the diaper 1 bows. In response to contraction of these elastic members 42, 32, the barrier cuff 20 is fully raised up from the topsheet 2 to maximize the space 51 as shown. In this state, the inner sheet 21 and the outer sheet 22 cooperate with each other to form the double wall structure. With the barrier cuff 20 fully raised up in this manner, the outer side edge 28 of the inner sheet 21 cooperates with the outer side edge 38 of the outer sheet 22 to define a bottom side edge, the inner side edge 39 of the outer sheet 22 defines a top side edge, and the inner side edge 29 of the inner sheet 21 defines a joint to the outer sheet 22. The barrier cuff 20 taking such posture effectively banks up body fluid flowing outward in the transverse direction of the diaper 1. Even if the inner sheet 21 is soiled with body fluid, the outer sheet 22 functions to conceal such soil from being highly visible. In addition, even if body fluid permeate the inner sheet 21, it is unlikely that such body fluid might leak out from the diaper 1 since such body fluid is reliably held by the outer sheet 22 within the space 51. With the diaper 1 put on the wearer's body, the inner sheet 21 and the outer sheet 22 always move integrally with each other and therefore it is unlikely that the space 51 might disappear. Consequentially, the outer sheet 22 can reliably conceal soil and, at the same time, prevent leakage of body fluid. The elastic member 42 exclusively for the inner side edge causes the inner side edge 39 of the outer sheet 22 to be shrunk and thereby to be formed with gathers (not shown). The elastic member 32 exclusively for the intermediate section causes the intermediate section 31 of the inner sheet 21 to be shrunk and thereby to be formed with gathers (not shown). These gathers function to prevent the inner and outer sheets 21, 22 from coming in close contact with each other when these sheets 21, 22 move closer to each other. The contamination concealing effect provided by the outer sheet 22 is ensured so far as these two sheets 21, 22 are kept to be spaced from each other. A height of such barrier cuff 20 can be easily increased by expanding a width dimension of the outer sheet 22. With the diaper 1 put on the wearer's body, a dimension m by which the inner sheet 21 and the outer sheet 22 are spaced from each other on the topsheet 2 is preferably in a range of 3 to 30 mm and a dimension n by which the barrier cuff 20 is raised up from the topsheet 2, i.e., a height from the topsheet 2 to the inner side edge 39 of the outer sheet 22 in FIG. 4 is preferably in a range of 10 to 100 mm.

Figure 5:
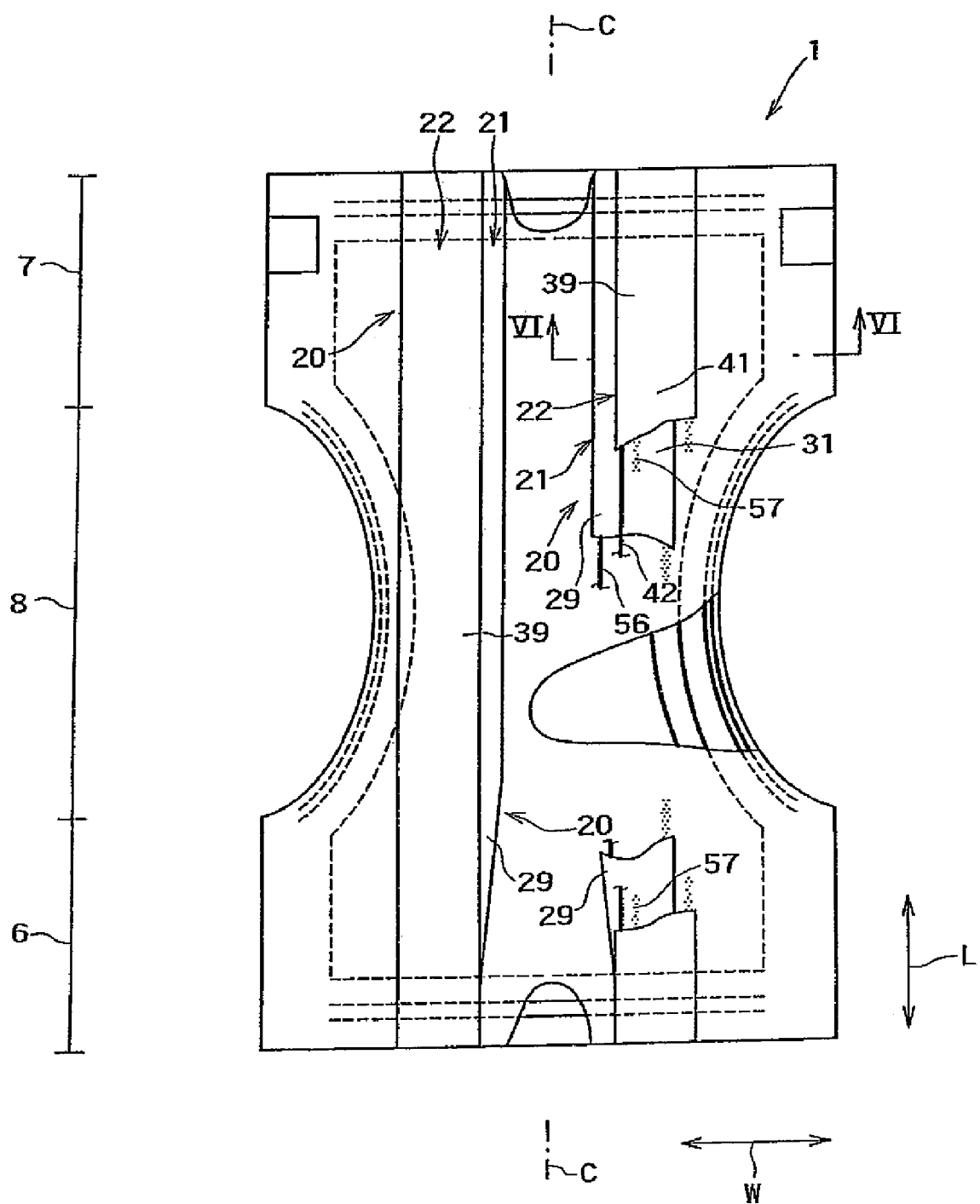
FIG. 5 is a view similar to FIG. 1, showing other embodiment of the present invention.
Figure 6:
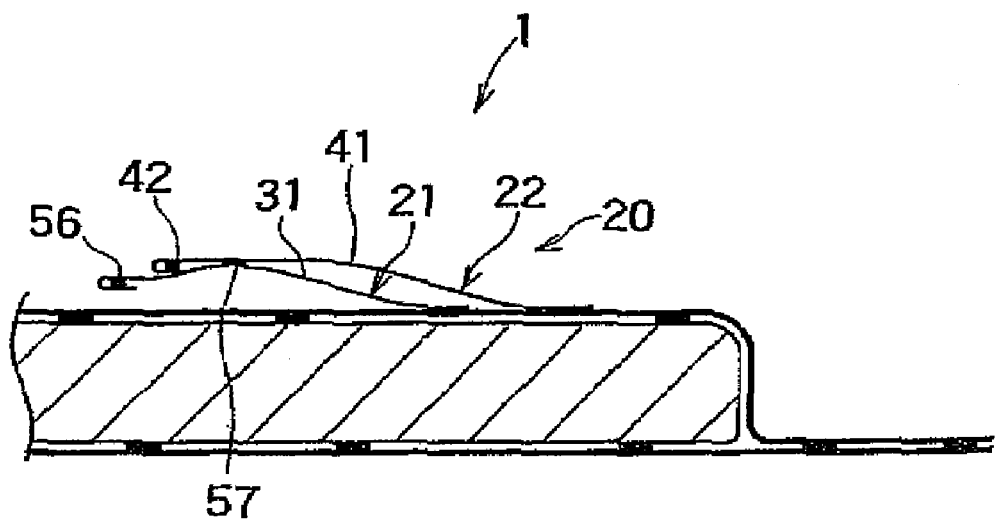
FIG. 6 is a sectional view taken along the line VI-VI in FIG. 5.
Figure 7:
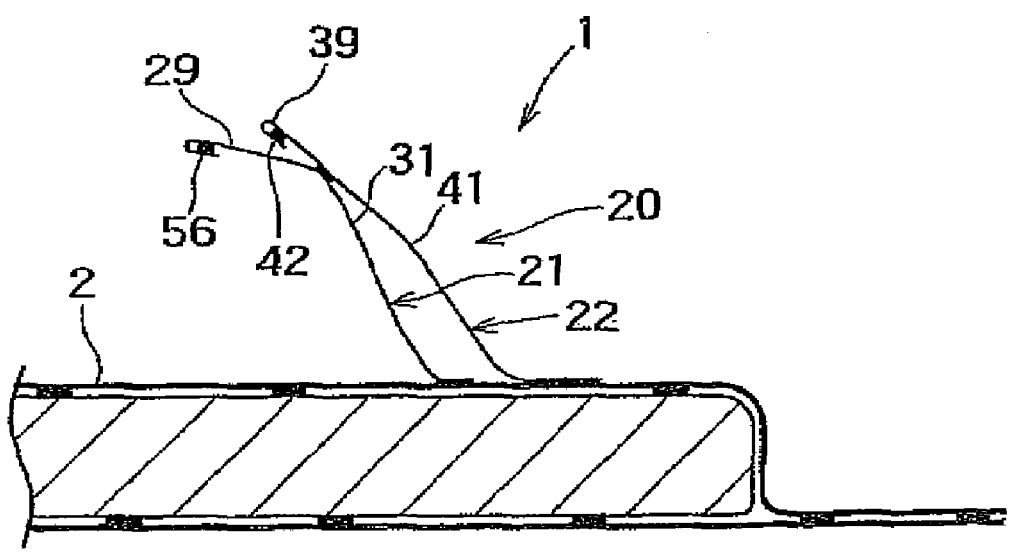
FIG. 7 is a view similar to FIG. 4, showing a posture taken by one of barrier cuffs when the disposable diaper of FIG. 5 bows.

FIGS. 5, 6 and 7 show other embodiment of the present invention, of which FIG. 5 is a view similar to FIG. 1, FIG. 6 is a sectional view taken along the line VI-VI in FIG. 5 and FIG. 7 is a view similar to FIG. 4, showing a posture taken by one of the barrier cuffs 20 when the disposable diaper 1 of FIG. 5 bows. As will be apparent from FIGS. 5 and 6, the inner sheet 21 of the barrier cuff 20 has its inner side edge 29 extends toward the center line C beyond the inner side edge 39 of the outer sheet 22 in the rear waist region 7 and the crotch region 8. It should be noted here that the inner sheet 21 extends obliquely with respect to the center line C as will be apparent from FIG. 5 so that a dimension by which the opposite inner side edges 29, 29 are spaced from each other may be maximized in a urination zone extending from the crotch region into the front waist region. The inner and outer sheets 21, 22 are bonded to each other in the respective intermediate sections 31, 41 by means of hot melt adhesive 57 while a second elastic member 56 exclusively for the inner side edge 29 is attached in a stretched state to the inner side edge 29 of the inner sheet 21. It should be noted here that the inner sheet 21 according to this embodiment is not provided with the elastic member 32 exclusively for the intermediate section 31 as seen in FIG. 3. The inner side edge 39 of the outer sheet 22 is provided with the elastic member 42 exclusively for the inner side edge 39 similar to that as seen in FIG. 3.

The first mentioned elastic member 42 exclusively for the inner side edge 39 as well as the second elastic member 56 exclusively for the inner side edge 29 contracts so as to raise up the barrier cuffs 20 as shown in FIG. 6 when the diaper 1 bows. Consequently, the respective inner side edges 29, 39 come in close contact with the wearer's skin under the effect of these elastic members 42, 56. As has previously been described, the dimension by which the inner side edges 29, 29 of the respective inner sheets 21, 21 is maximized in the urination zone (See FIG. 5) so that urine discharged from the wearer can be reliably absorbed by the core 4 between the barrier cuffs 20. In this regard, it is possible without departing from the scope of the present invention to adopt, in the diaper 1 of FIG. 5, a pair of barrier cuffs arranged in a manner that the inner side edges 29, 29 extend not obliquely with respect to the center line C but in parallel to each other.

The diaper 1 of such construction may be exploited using stock materials as will be described. The liquid-pervious topsheet 2 may be formed from a stock material selected from the group including a nonwoven fabric and a perforated plastic film. The liquid-impervious backsheet 3 may be formed from a stock material selected from the group including a plastic film, a nonwoven fabric and a composite sheet comprising a plastic film and a nonwoven fabric laminated together. The core 4 may be formed from a stock material fluff pulp fibers or a mixture of fluff pulp fibers and super-absorbent polymer particles, in any case, wrapped with a sheet having a high liquid-permeability such as a tissue paper or a nonwoven fabric or a sheet having a high liquid-permeability as well as a high liquid-spreadability. The inner sheet 21 as well as the outer sheet 22 constituting the barrier cuff 20 may be formed from a water-repellent, preferably water-repellent and liquid-impervious sheet in the form of nonwoven fabric or plastic film. In the case of one embodiment wherein sheet material having an air-permeability higher than that of the inner sheet 21 is used as the outer sheet 22, it is also possible without departing from the scope of the present invention to use the inner and outer sheets 21, 22 which are different from each other in terms of an air-permeability, a flexibility and the other properties. Furthermore, it is possible without departing from the scope of the present invention to weld the sheets together instead of bonding them by means of adhesive or vice versa. It is also possible to exploit the present invention not only in the form of the open-type diaper as illustrated but also in the form of the pants-type or pull-on diaper.

The present invention allows it possible to make the disposable diaper wherein a height of the double wall barrier cuffs can be easily increased.

The entire discloses of Japanese Patent Application No. 2005-322567 filed on Nov. 7, 2005 including specification, drawings and abstract are herein incorporated by reference in its entirety.

What is claimed is:

1. A disposable diaper having a front waist region, a rear waist region and a crotch region extending in a longitudinal direction of the diaper between said waist regions, said disposable diaper comprising:

an inner surface adapted to contact a wearer's skin, an outer surface adapted to contact the wearer's undergarment, a body fluid absorbent core interposed between said inner and outer surfaces, and a pair of elastic barrier cuffs extending from said crotch region into said front and rear waist regions and adapted to be raised up from said inner surface, each of said barrier cuffs comprising first and second sheet strips provided separately of each other, said first and second sheet strips respectively comprising bottom side edges fixed to said inner surface in said front and rear waist regions as well as in said crotch region, and top side edges free of direct attachment to said inner surface at least in said crotch region, wherein said bottom side edge of said first sheet strip is inwardly spaced, in a transverse direction of the diaper, from said bottom side edge of said second sheet strip, said top side edges of said first and second sheet strips are disposed inboard of the respective bottom side edges, and one of said top side edges is spaced inwardly in the transverse direction from the other, the top side edge of said second sheet strip is provided with an elastic member extending in the longitudinal direction and bonded in stretched state thereto, and said first and second sheet strips are directly bonded to each other in vicinities of the top side edges thereof;

wherein the top side edge of the second sheet strip along which the elastic member is bonded is moveable independently of the top side edge of the first sheet strip;

the first sheet strip has a first section defined between a bonding site, where said first sheet strip and said second sheet strip are directly bonded to each other, and the top side edge of the first sheet strip;

the second sheet strip has a second section defined between said bonding site and said elastic member bonded along the top side edge of the second sheet strip; and a width of said first section as measured in the transverse direction is smaller than that of the second section, whereby said top side edge of said second sheet strip extends inward in the transverse direction beyond said top side edge of said first sheet strip.

2. The diaper defined by claim 1, wherein said second section of said second sheet strip is moveable independently of and relative to the first section of said first sheet strip in both the transverse direction and a thickness direction of the absorbent core.

3. The diaper defined by claim 2, wherein the first sheet strip has a third section defined between said bonding site and the bottom side edge of the first sheet strip, where the first sheet strip is bonded to the inner surface of the diaper;

the second sheet strip has a fourth section defined between said bonding site and the bottom side edge of the second sheet strip, where the second sheet strip is bonded to the inner surface of the diaper; and a width of said third section as measured in the transverse direction is smaller than that of the fourth section.

4. The diaper defined by claim 2, further comprising a further elastic member extending in the longitudinal direction and bonded in stretched state to a middle zone of the third section of the first sheet strip;

said further elastic member being different from the elastic member bonded to the top side edge of said second sheet strip.

5. The diaper defined by claim 2, wherein the first and second sheet strips have different air permeabilities or flexibilities.

* * * * *